United States Patent [19]

Déziel et al.

[11] Patent Number: 5,476,841
[45] Date of Patent: Dec. 19, 1995

[54] INHIBITORS OF HERPES VIRAL RIBONUCLEOTIDE REDUCTASE

[75] Inventors: Robert Déziel, Mont-Royal; Neil Moss, Laval, both of Canada

[73] Assignee: Bio-Mega/Boehringer Ingelheim Research Inc., Laval, Canada

[21] Appl. No.: 203,086

[22] Filed: Feb. 28, 1994

Related U.S. Application Data

[63] Continuation-in-part of Ser. No. 25,540, Mar. 3, 1993, abandoned.

[51] Int. Cl.$^6$ .......................... A61K 38/00; C07K 7/00; C07K 5/00; C07K 17/00
[52] U.S. Cl. .......................... 514/17; 530/329; 530/330
[58] Field of Search .......................... 530/329, 330; 514/17

[56] References Cited

FOREIGN PATENT DOCUMENTS 0411334  2/1991  European Pat. Off. .
0438873  7/1991  European Pat. Off. .

OTHER PUBLICATIONS

Chang et al. Bioorganic & Medicinal Chem. Lett. vol. 2, p. 1207 (1992).

*Primary Examiner*—Jill Warden
*Assistant Examiner*—Sheela J. Huff
*Attorney, Agent, or Firm*—R. P. Raymond; M-E. M. Devlin; W. E. Rieder

[57] ABSTRACT

Peptide derivatives are of the formula A—B—D—NHCH{CH$_2$C(O)R$^1$}C(O)—NHCH{CR$^2$(R$^3$)—COOH}C(O)—E wherein A is a lower alkanoyl bearing two substituents, each substituent selected independently from phenyl or a monosubstituted phenyl wherein the monosubstituent is alkyl, halo, hydroxy or alkoxy; B is a N-methyl amino acid residue; D is an amino acid residue; R$^1$ is alkyl, cycloalkyl, a monosubstituted amino or a disubstituted amino; R$^2$ is hydrogen or alkyl and R$^3$ is alkyl, or R$^2$ and R$^3$ are joined to form a cycloalkyl; and E is a terminal unit, for example, an alkylamino or a monovalent amino acid radical such as NHCH(alkyl)C(O)OH. The derivatives are useful for treating herpes infections.

14 Claims, No Drawings

INHIBITORS OF HERPES VIRAL RIBONUCLEOTIDE REDUCTASE

This application is a continuation-in-part of Ser. No. 08/025540, filed Mar. 3, 1993, now abandoned.

FIELD OF THE INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to methods of using the peptides to inhibit the replication of herpes virus and to treat herpes infections.

BACKGROUND OF THE INVENTION

Herpes viruses inflict a wide range of diseases against humans and animals. For instance; herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital herpes simplex infections.

Nevertheless, in spite of some significant advances, the need for effective, safe therapeutic agents for treating herpes viral infections continues to exist. For a review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The selective action of these peptides against herpes viruses, combined with a wide margin of safety, renders the peptides as desirable agents for combating herpes infections.

The following references disclose peptides or peptide derivatives which have been associated with anti-herpes activity:

B. M. Dutia et al., Nature, 321, 439 (1986),
E. A. Cohen et al., Nature, 321, 441 (1986),
J. H. Subak-Sharpe et al., UK patent application 2185024, published Jul. 8, 1987,
P. Gaudreau et al., J. Biol. Chem., 262, 12413 (1987),
E. A. Cohen et al., U.S. Pat. No. 4,795,740, Jan. 3, 1989,
R. Freidinger et al., U.S. Pat. No. 4,814,432, Mar. 21, 1989,
V. M. Garskey et al., U.S. Pat. No. 4,837,304, Jun. 6, 1989,
R. Colonno et al., U.S. Pat. No. 4,845,195, July 4, 1989,
P. Gaudreau et al., J. Med. Chem., 33, 723 (1990),
J. Adams et al., European patent application 408,973, published Jan. 23, 1991,
P. L. Beaulieu et al., European patent application 411,332, published Feb. 6, 1991,
J. Adams et al., European patent application 411,333, published Feb. 6, 1991,
J. Adams et al., European patent application 411,334, published Feb. 6, 1991,
R. L. Tolman et al., European patent application 412, 595, published Feb. 13, 1991,
W. T. Ashton et al., European patent application 438,873, published Jul. 31, 1991,
P. L. Beaulieu et al., European patent application 461,546, published Dec. 18, 1991,
P. Gaudreau et al., J. Med. Chem., 35, 346 (1992),
R. Déziel and Y. Guindon, Canadian patent application 2,033,448, published Jul. 1, 1992, and L. L. Chang et al., Biorganic & Medicinal Chemistry Letters, 2, 1207 (1992).

The subject peptides of the previous reports can be distinguished from the peptides of the present application by characteristic structural and biological differences.

Abbreviations and symbols used hereinafter are defined in the "Details of the Invention" section of this application.

SUMMARY OF THE INVENTION

The peptides of this invention are represented by formula 1

$$A-B-D-NHCH\{CH_2C(O)R^1\}C(O)-$$
$$NHCH\{CR^2(R^3)C(O)OH\}C(O)-E$$

wherein

A is a disubstituted lower alkanoyl wherein each of the substituents is selected independently from the group consisting of phenyl and monosubstituted phenyl wherein the monosubstituent is selected from the group consisting of lower alkyl, halo, hydroxy and lower alkoxy;

B is $N(CH_3)CHR^4C(O)$ wherein $R^4$ is lower alkyl; D is $NH-CHR^5C(O)$ wherein $R^5$ is lower alkyl or a lower alkyl monosubstituted with carboxy, hydroxy, mercapto or benzyloxy;

$R^1$ is lower alkyl, lower cycloalkyl, {1-(lower alkyl)-(lower cycloalkyl)}, or $NR^6R^7$ wherein $R^6$ is hydrogen or lower alkyl and $R^7$ is lower alkyl, or $R^6$ and $R^7$ together with the nitrogen atom to which they are attached form a pyrrolidino, piperidino, morpholino or 4-methylpiperazino;

$R^2$ is hydrogen or lower alkyl and $R^3$ is lower alkyl, or $R^2$ and $R^3$ together with the carbon atom to which they are attached form a lower cycloalkyl; and E is $NHR^8$ wherein $R^8$ is (4–9C)alkyl; lower cycloalkyl; lower cycloalkyl monosubstituted or disubstituted with lower alkyl or (lower alkyl)-(lower cycloalkyl); or E is $NHCH(R^9)-Z$ wherein $R^9$ is (4–9C)alkyl, lower cycloalkyl or (lower cycloalkyl)-(lower alkyl) and Z is $CH_2OH$, $C(O)OH$, $C(O)NH_2$ or $C(O)OR^{10}$ wherein $R^{10}$ is lower alkyl;

or a therapeutically acceptable salt thereof.

A preferred group of the peptides of this invention is represented by formula 1 wherein A is lower alkanoyl disubstituted with phenyl, 4-(lower alkyl)phenyl, 4-halophenyl or 4-(lower alkoxy)phenyl; B is (N-Me)Val, (N-Me)Ile or (N-Me)Tbg; D is amino acid residue of (S)-2-amino-3-hydroxy-3-methylbutyric acid or (R)-2-amino-3-mercapto-3-methylbutyric acid or an amino acid residue selected from Val, Ile and Tbg; $R^1$ is lower alkyl, lower cycloalkyl, {1-(lower alkyl)-(lower cycloalkyl)}, N,N-dimethylamino, N,N-diethylamino, pyrrolidino or morpholino; $R^2$ and $R^3$ are as defined hereinabove; and E is $NHR^8$ wherein $R^8$ is (4–9C)alkyl; lower cycloalkyl; lower cycloalkyl monosubstituted or disubstituted with lower alkyl; or (lower alkyl)-(lower cycloalkyl); or E is $NHCH(R^9)-Z$ wherein $R^9$ is (4–9C)alkyl or (lower cycloalkyl)methyl and Z is as defined hereinabove; or a therapeutically acceptable salt thereof.

A more preferred group of the peptides is represented by formula 1 wherein A is 2-(phenylmethyl)-3-phenylpropionyl, 2-{(4-fluorophenyl)methyl}-3-(4-fluorophenyl)propionyl, 2-{(4-methoxyphenyl)methyl}-3-phenylpropionyl or 2-{(4-methoxyphenyl)methyl}-3-(4-methoxyphenyl)propionyl; B is (N-Me)-Val or (N-Me)-Ile; D is Val, Ile or Tbg; $R^1$ is 1-methylethyl, 1,1-dimethylethyl, 1,1-dimethylpropyl, cyclobutyl, cyclopentyl, cyclohexyl, 1-methylcyclopentyl, N,N-dimethylamino, N,N-diethylamino, pyrrolidino or morpholino; $R^2$ is hydrogen and $R^3$ is methyl, ethyl, 1-methylethyl, 1,1-dimethylethyl or propyl, and the carbon atom bearing $R^2$ and $R^3$ has the (R)-configuration, or $R^2$ and $R^3$ each independently is methyl or ethyl, or $R^2$ and $R^3$ together with the carbon atom to which they are attached form a cyclobutyl, cyclopentyl or cyclohexyl; and E is $NHR^8$ wherein $R^8$ is 2,2-dimethylpropyl, 1(R),2,2-trimethylpropyl, 1(R)-ethyl-2,2-dimethylpropyl, 2,2-dimethylbutyl, 3,3-dimethylbutyl, 1(R),2,2-trimethylbutyl, 1(R),3,3-trimethylbutyl, 1(R)-ethyl-3,3-dimethyl, or cyclohexylmethyl; or E is $NHCH(R^9)$—Z wherein the carbon atom bearing $R^9$ has the (S)-configuration, $R^9$ is 11-dimethylethyl, 1-methylpropyl, 2-methylpropyl, 2,2-dimethylpropyl or cyclohexylmethyl and Z is $CH_2OH$, $C(O)OH$, $C(O)NH_2$ or $C(O)OR^{10}$ wherein $R^{10}$ is methyl, ethyl or propyl; or a therapeutically acceptable salt thereof.

A most preferred group of the peptides is represented by formula 1 wherein A is 2-(phenylmethyl)-3-phenylpropionyl; B is (N-Me)Val; D is Tbg; $R^1$ is 1-methylethyl, 1,1-dimethylethyl, 1-methylpropyl, 1,1-dimethylpropyl, 2,2-dimethylpropyl, cyclobutyl, cyclopentyl, cyclohexyl, 1-methylcyclopentyl, pyrrolidino or morpholino; $R^2$ is hydrogen and $R^3$ is methyl, ethyl, 1-methylethyl or propyl, and the carbon atom bearing $R^2$ and $R^3$ has the (R)-configuration, or $R^2$ and $R^3$ each independently is methyl or ethyl, or $R^2$ and $R^3$ together with the carbon atom to which they are attached form a cyclobutyl, cyclopentyl or cyclohexyl; and E is $NHR^8$ wherein $R^8$ is 2,2-dimethylpropyl, 1(R),2,2-trimethylpropyl, 1(R)-ethyl-2,2-dimethylpropyl, 2,2-dimethylbutyl or 1(R)-ethyl-3,3-dimethylbutyl, or E is $NHCH(R^9)$—Z wherein the carbon atom bearing $R^9$ has the (S)-configuration, $R^9$ is 2,2-dimethylpropyl and Z is $CH_2OH$, $C(O)OH$, $C(O)NH_2$ or $C(O)OR^{10}$ wherein $R^{10}$ is methyl, ethyl or propyl; or a therapeutically acceptable salt thereof.

Included within the scope of this invention is a pharmaceutical composition comprising an anti-herpes virally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the peptide of formula 1, or a therapeutically acceptable salt thereof.

Another important aspect involves a method of inhibiting the replication of herpes virus by contacting the virus with a herpes viral ribonucleotide reductase inhibiting amount of the peptide of formula 1, or a therapeutically acceptable salt thereof.

Still another aspect involves a method of treating a herpes viral infection in a mammal by administering thereto an anti-herpes virally effective amount of a combination of the peptide of formula 1, or a therapeutically acceptable salt thereof, and an antiviral nucleoside analog. A pharmaceutical composition comprising the combination is also within the scope of this invention.

Processes for preparing the peptides of formula 1 are described hereinafter.

DETAILS OF THE INVENTION

GENERAL

Alternatively, formula 1 can be illustrated as:

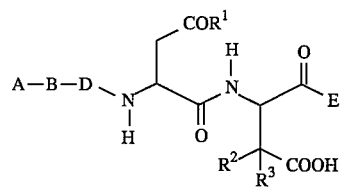

The term "residue" with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Val, Ile, Asp, and Leu represent the residues of L-valine, L-isoleucine, L-aspartic acid and L-leucine, respectively.

The asymmetric carbon atoms residing in the principal linear axis (i.e. the backbone) of the peptides of formula 1, exclusive of the terminal groups A and Z (of E) but including the carbon atom bearing "$R^9$" when E is $NHCH(R^9)$—Z as defined herein, have an S configuration.

Asymmetric carbon atoms residing in the side chain of an amino acid or derived amino acid residue, in the terminal group A, and in the terminal group E when E represents $NHR^8$ as defined herein, may have the S or R configuration.

The symbol "Tbg" represents the amino acid residue of (S)-2-amino-3,3-dimethylbutanoic acid. The symbol "γMeLeu" represents the amino acid residue of (S)-2-amino-4,4-dimethylpentanoic acid. The symbol "γMeLeucinol" represents (S)-2-amino-4,4-dimethylpentanol with one hydrogen removed from the α-amino group.

Other symbols used herein are: (N-Me)Val for the residue of (S)-3-methyl-2-(methylamino)butanoic acid; (N-Me)Ile for the residue of (S)-3-methyl-2-(methylamino)pentanoic acid; (N-Me)Tbg for the residue of (S)-2-(methylamino)-3,3-dimethyl butanoic acid; Asp(cyBu) for the residue of (S)-α-amino-1-carboxycyclobutaneacetic acid; Asp(cyPn) for the residue of (S)-α-amino-1-carboxycyclopentaneacetic acid; and Asp{(R)-Me} for the residue of 3-(R)-methyl-L-aspartic acid (i.e. {S-(R*,S*)}-2-amino-3-methylbutanedioic acid).

The term "halo" as used herein means a halo radical selected from bromo, chloro, fluoro or iodo.

The term "lower alkanoyl" as used herein means a straight chain 1-oxoalkyl containing from two to six carbon atoms or a branched chain 1-oxoalkyl containing from four to six carbon atoms; for example, acetyl, propionyl(1-oxopropyl) and 2-methyl-1-oxopropyl.

The term "(4–9 C)alkyl" as used herein means straight and branched chain alkyl radicals containing from four to nine carbon atoms and includes, for example, 1-methylpropyl, 2-methylpropyl, 2,2-dimethylpropyl, 1,2,2-trimethylpropyl, 3,3-dimethylbutyl, 1-ethyl-2,2-dimethylbutyl and 4,4-dimethylpentyl.

The term "lower alkyl" as used herein, either alone or in combination with another radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "{1-(lower alkyl)-(lower cycloalkyl)}" as used herein means a lower cycloalkyl radical bearing a lower alkyl substituent at position 1; for example, 1-ethylcyclopropyl, 1-propylcyclopentyl and 1-propylcyclohexyl.

The term "lower cycloalkyl" as used herein, either alone or in combination with another radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of peptide chemistry; for instance, E. Schröder and K. L. Lübke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are diphenylphosphoryl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole. Still another very practical and useful coupling agent is the commercially available 2-(1H-benzotriazol-1-yl)-N,N, N', N'-tetramethyluronium tetrafluoroborate.

Process

The peptides of formula 1 can be prepared by processes which incorporate therein methods commonly used in peptide synthesis such as the classical solution coupling of amino acid residues and/or peptide fragments. Such methods are described, for example, by E. Schröder and K. Lübke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues (or, if required, non-peptidic fragments of the peptide) with suitable protective groups which will prevent a chemical reaction from occurring at that site until the protective group is ultimately removed. Also common is the protection of an α-amino group on an amino acid or a fragment while that entity reacts at the carboxy group, followed by the selective removal of the α-amino protective group to allow subsequent reaction to take place at that location. Another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling, in the order of the sequence of the peptide, of the appropriate amino acid or derived amino acid residues, and non-peptidic fragments of the peptide (such as the key intermediates), which if required are suitably protected, and eliminating all protecting groups, if present, at the completion of the stepwise coupling to obtain the peptide of formula 1. More specific processes are illustrated in the examples hereinafter.

Most of the intermediates and processes for preparing same have been described by J. Adams et al., European patent application 411 332, published Feb. 6, 1991, J. Adams et al., European patent application 411,334, published Feb. 6, 1991 and by R. Déziel and Y. Guindon, Canadian patent application 2,033,448, published Jul. 1, 1992.

The lower alkanoic acids disubstituted with phenyl or a monosubstituted phenyl, required for the elaboration of the N-terminus of the present peptides are known or can be prepared by known methods; for example, see L. L. Chang et al., Bioorganic & Medicinal Chemistry Letters, 2, 1207 (1992). Dibenzylacetic acid has been described by M. R. Dolique, Ann. Chim. (Paris), 15 (10), 425 (1931) and by F. Krollpfeiffer and A. Rosenberg, Chem. Ber., 69, 465 (1936).

The peptide of formula 1 of this invention can be obtained in the form of a therapeutically acceptable salt. In the instance where a particular peptide has a residue which functions as a base, examples of such salts of the base are those with organic acids, e.g. acetic, lactic, succinic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts of the carboxy group are those with the sodium, potassium or calcium cations, or with organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV) and Epstein-Barr virus (EBV).

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, R. Déziel and Y. Guindon, Canadian patent application 2,033,488, published Jul. 1, 1992.

The therapeutic effect of the peptides can be demonstrated in laboratory animals, for instance, by using an assay based on the murine model of herpes simplex virus-induced ocular disease for antiviral drug testing, described by C. R. Brandt et al., J. Virol. Meth., 36, 209 (1992).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 5 percent, preferably 0.5 to 2 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 18th ed, Mack Publishing Company, Easton, Pa., 1990.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an amount sufficient to cover the infected area. The treatment should be repeated, for example, every four to six hours until lesions heal.

With reference to systemic administration, the peptide of formula 1 is administered at a dosage of 10 µg to 500 µg per kilogram of body weight per day, although the aforementioned variations will occur. However, a dosage level that is in the range of from about 10 µg to 200 µg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove are indicated to be effective and relatively safe medications for treating herpes viral infections, the possible concurrent administration of these formulations with other antiviral medications or agents to obtain beneficial results is not excluded. Such other antiviral medications or agents include the antiviral nucleosides, for example, acyclovir, and antiviral surface active agents or antiviral interferons such as those disclosed by S. S. Asculai and F. Rapp in U.S. Pat. No. 4,507,281, Mar. 26, 1985.

More specifically with respect to treating herpes viral infections by concurrent administration, it has been found that the anti-herpes activity of an antiviral nucleoside analogs can be enhanced synergistically, without the concomitant enhancement of toxic effects, by combining the same with a peptide of formula 1. Accordingly, there is provided herewith a pharmaceutical composition for treating herpes infections in a mammal comprising a pharmaceutically or veterinarily acceptable carrier, and an effective amount of the combination of an antiviral nucleoside analog or a therapeutically acceptable salt thereof, and a ribonucleotide reductase inhibiting peptide of formula 1 or a therapeutically acceptable salt thereof.

Also provided herein is a method of treating herpes viral infections in a mammal. The method comprises administering to the mammal an anti-herpes virally effective amount of a combination of a compound of formula 1 or a therapeutically acceptable salt thereof, and an antiviral nucleoside analog or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 2

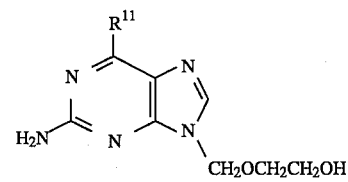

wherein $R^{11}$ is hydrogen, hydroxy or amino, or a therapeutically acceptable salt thereof. (Formula 2 wherein $R^{11}$ is hydroxy represents acyclovir.)

Other preferred antiviral nucleoside analogs for use according to the present invention include vidarabine, idoxuridine, trifluridine, ganciclovir, edoxudine, brovavir, fiacitabine, penciclovir, famciclovir and rociclovir.

The term "synergistic effect" when used in relation to the antiviral or anti-herpes activity of the above defined combination of the nucleoside analog and peptide of formula 1 means an antiviral or anti-herpes effect which is greater than the predictive additive effect of the two individual components of the combination.

When utilizing the combination of this invention for treating herpes infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the peptide of formula 1, chosen route of administration, standard biological practice, and by the relative amounts of the two active ingredients to provide a synergistic antiviral effect. Preferably, the combination is administered topically. For example, the two active agents (i.e. the antiviral nucleoside analog and the peptide of formula 1, or their therapeutically acceptable salts) can be formulated in the form of solutions, emulsions, creams, or lotions in pharmaceutically acceptable vehicles. Such formulation can contain 0.01 to 1.0 percent by weight of the nucleoside analog, or a therapeutically acceptable salt thereof, and about 0.05 to 1 percent by weight of the peptide of formula 1, or a therapeutically acceptable salt thereof.

In any event, the two active agents are present in the pharmaceutical composition in amounts to provide a synergistic anti-herpes effect.

The following examples illustrate further this invention. Temperatures are given in degrees Celsius. Solution percentages or ratios express a volume to volume relationship, unless stated other wise. Nuclear magnetic resonance spectra were recorded on a Bruker 200 or 400 MHz spectrometer, (a 400 MHz spectrum being noted in the preamble); the chemical shifts (δ) are reported in parts per million. Abbreviations used in the examples include Boc: tert-butyloxycarbonyl; Bzl: benzyl; EtOH: ethanol; EtOAc: ethyl acetate; $Et_2O$: diethyl ether; HPLC: high performance liquid chromatography; MeOH: methanol; THF: tetrahydrofuran.

EXAMPLE 1

General Procedure for Coupling Reactions
{See also R. Knorr et al., Tetrahedron Letters, 30, 1927 (1989).}

The first reactant, i.e. a free amine (or its hydrochloride salt), is dissolved in $CH_2Cl_2$ or acetonitrile and the solution is cooled to 4°. Under a nitrogen atmosphere, four equivalents of N-methylmorpholine is added to the stirred solution. After 20 min., one equivalent of the second reactant, i.e. a free carboxylic acid, and 1.05 equivalent of the coupling agent are added. (Practical and efficient coupling reagents for this purpose are (benzotriazol-1-yloxy)tris(dimethylamino)phosphonium hexafluorophosphate or preferably 2-(1H-benzotriazol-1-yl)-N,N,N',N'-tetramethyluronium tetrafluoroborate. The reaction is monitored by TLC. After completion of the reaction, the $CH_2Cl_2$ (or acetonitrile) is evaporated under reduced pressure. The residue is dissolved in EtOAc. The solution is washed successively with 1N aqueous citric acid, 10% aqueous $Na_2CO_3$ and brine. The organic phase is dried ($MgSO_4$), filtered and concentrated to dryness under reduced pressure. The residue is purified on silica gel ($SiO_2$) according to Still's flash chromatography technique {W. C. Still et al., J. Org. Chem., 43, 2923 (1978)}.

EXAMPLE 2

Preparation of the Intermediate
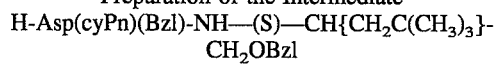

(a) (S)-α-Azido-1-{(phenylmethoxy)carbonyl}-cyclopentaneacetic acid: This compound was prepared from 2-oxospiro[4.4]nonane-1,3-dione, described by M. N. Aboul-Enein et al., Pharm. Acta Helv., 55, 50 (1980), according to the asymmetric azidation method utilizing the Evan's auxiliary, see D. A. Evans et al., J. Amer. Chem. Soc., 112, 4011 (1990).

More explicitly, a 1.6M hexane solution of butyllithium (469 ml, 750 mmol) was added dropwise under an argon atmosphere to a solution of the chiral auxiliary, 4(S)-(1-methylethyl)-2-oxazolidinone, {96.8 g, 750 mmol, described by L. N. Pridgen and J. Prol., J. Org. Chem., 54, 3231 (1989)} in dry THF at −40°. The mixture was stirred at −40° for 30 min and then cooled to −78°. 2-Oxospiro [4.4]nonane-1,3-dione was added dropwise to the cooled mixture. The mixture then was stirred at 0° for 1 h. Thereafter, a 20% (w/v) aqueous solution of citric acid (600 mL) was added to the mixture. The organic phase was separated and the aqueous phase was extracted with EtOAc. The combined organic phases were washed with brine, dried ($MgSO_4$) and concentrated under reduced pressure to give 3-{2-(1-carboxycyclopentyl)-1-oxoethyl)}-4(S)-(1-methylethyl)-2-oxazolidinone as a pink solid (300 g).

The latter solid (ca 750 mmol) was dissolved in acetonitrile (1 L). Benzyl bromide (128.3 g, 89.2 mL, 750 mmol) and 1,8-diazabicyclo[5.4.0]-undec-7-ene (114 g, 112 mL, 750 mmol) were added to the solution. The mixture was stirred under argon for 16 h. The volatiles were removed under reduced pressure. The residue was dissolved in $H_2O$/EtOAc. The organic phase was separated, washed with a 10% (w/v) aqueous solution of citric acid, brine, dried ($MgSO_4$) and concentrated to dryness under reduced pressure to give an oil. Crystallization of the oil from hexane/EtOAc gave the corresponding benzyl ester as a white solid (204 g, 73%).

A solution of the latter compound (70 g, 187 mmol) in dry THF (200 mL) was cooled to −78°. A 0.66M THF solution of potassium 1,1,1,3,3,3-hexamethyldisilazane (286 mL, 189 mmol) containing 6% (w/v) cumene was added over a period of 15 min to the cooled solution. The mixture was stirred at −78° for 45 min. A solution of 2,4,6-triisopropylbenzenesulfonyl azide (67 g, 216 mmol) in dry THF (100 mL) was added in one portion to the cold mixture, followed two minutes later by the addition of glacial acetic acid (50 mL, 860 mmol). The mixture was warmed and stirred at 35°–45° for 1 h. The volatiles were removed under reduced pressure. The yellow residue was triturated with hexane/EtOH (4:1, 1.7 L). The resulting white solid was collected on a filter. The filtrate was mixed with $SiO_2$ (230–240 mesh). Volatiles were removed under reduced pressure and the residual solid was dried at 35° under reduced pressure to remove cumene. The residual solid then was placed on a column of $SiO_2$. Elution of residual solid and $SiO_2$ with hexane-EtOAc, 9:1 and concentration of the eluent gave 3-{{2(S)-azido-1-oxo- 2-{1-{(phenylmethoxy)-carbonyl}cyclopentyl}-ethyl}-4(S)-(1-methylethyl)-2-oxazolidinone (66 g, 86%).

A solution of the latter compound (13.42 g, 32.4 mmol) in THF/H$_2$O (3:1, 608 mL) was cooled to 0°. Hydrogen peroxide/H$_2$O (3:7, 16.3 mL, 518 mmol of H$_2$O$_2$) was added to the cooled solution; followed by the addition of LiOH.H$_2$O (2.86 g, 68.2 mmol). The mixture was stirred at 0° for 45 min and then quenched with a 10% (w/v) aqueous solution of sodium sulfite (400 mL). After NaHCO$_3$ (1.93 g) had been added, the mixture was concentrated under reduced pressure. The chiral auxiliary was recovered by continuous extraction (aqueous NaHCO$_3$/chloroform) for 20 h. Thereafter, the aqueous phase was cooled to 0° rendered acidic by the addition of concentrated HCl and then extracted with EtOAc. The extract was washed with brine, dried (MgSO$_4$) and concentrated under reduced pressure to give the desired compound as a white solid (8.2 g, 84%). The $^1$H NMR (CDCl$_3$) of the compound showed: δ1.6–1.8 (m, 5H), 1.95–2.05 (m, 2H), 2.20–2.30 (m, 1H), 4.55 (s, 1H), 5.12 (s, 2H) and 7.4 (m, 5H).

The compound is used in section (c) of this example.

(b) NH$_2$—(S)—CH{CH$_2$C(CH$_3$)$_3$}CH$_2$Obzl: H-γMeLeu-OH was reduced with LiBH$_4$/Me$_3$SiCl according to the method of A. Giannis and K. Sandhoff, Angew. Chem. Int. Ed. Engl., 28, 218 (1989) to give the aminoalcohol NH$_2$—(S)—CH{CH$_2$C(CH$_3$)$_3$}CH$_2$OH. A mixture of the latter compound (812 mg, 6.2 mmol), triethylamine (659 mg, 6.51 mmol) and di-tert-butyl dicarbonate (1.42 g, 6.51 mmol) in dry THF (15 mL) was stirred under a nitrogen atmosphere at 4° for 15 min and then at room temperature for 4 h. The THF was evaporated under reduced pressure. The residue was dissolved in EtOAc. The solution was washed with 10% aqueous citric acid, 5% aqueous NaHCO$_3$ and brine. The organic phase was dried (MgSO$_4$) and concentrated to dryness under reduced pressure. The residue was purified by flash chromatography (SiO$_2$, eluent: hexane-EtOAc, 2:1) to give Boc-NH—(S)—CH{CH$_2$C(CH$_3$)$_3$}CH$_2$OH (1.23 g, 86%).

Tetrabutylammonium bisulfate (106 mg) and 50% aqueous NaOH (3 mL) were added successively to a solution of Boc-NH—(S)—CH{CH$_2$C(CH$_3$)$_3$}CH$_2$OH (1.23 g, 5.35 mmol) in benzyl chloride (13 mL). The resulting mixture was stirred at 35°–40° for 90 min, diluted with EtOAc, and washed with H$_2$O and brine. The organic phase was dried (MgSO$_4$) and volatiles were removed under reduced pressure. The residue was dissolved in hexane. The solution was poured onto a column of SiO$_2$. The column was eluted with hexane to remove benzyl chloride, and then with hexane-EtOAc (2:1) to give Boc-NH—(S)—CH{CH$_2$C(CH$_3$)$_3$}CH$_2$OBzl. The $^1$H NMR (CDCl$_3$) of the latter compound showed δ0.95 (s, 9H), 1.42 (s, 9H), 1.30–1.55 (m, 2H), 3.42 (d, J=4 Hz, 2H), 3.88 (broad, 1H), 4.54 (m, 3H), 7.23–7.4 (m, 5H). The latter compound (1.28 g, 3.99 mmol) was dissolved in 6N HCl/dioxane (10 mL). The solution was stirred under a nitrogen atmosphere at 4° for 45 min. Evaporation of the solvent gave the hydrogen chloride salt of the desired compound (1.05 g). The compound is used without further purification in the next section of this example.

(c) The title compound of this example: By following the coupling procedure of example 1 and using the hydrogen chloride salt of NH$_2$—(S)—CH{CH$_2$C(CH$_3$)$_3$}CH$_2$OBzl of the preceding section as the first reactant and (S)-α-azido-1{(phenylmethoxy)carbonyl}cyclopentaneacetic acid of section (a) of this example as the second reactant, N-{(S)-1-benzyloxymethyl-3,3-dimethylbutyl}-(S)-α-azido-1-{(phenylmethoxy)carbonyl}cyclopentaneacetamide was obtained. Reduction of the latter compound with tin(II) chloride in MeOH according to the method of N. Maiti et al., Tetrahedron Letters, 27, 1423 (1986) gave the title compound of this example. The $^1$H NMR (CDCl$_3$) of the compound showed α0.98 (s, 9H), 1.22–2.25 (m, 12H), 3.4 (d, J=4 Hz, 2H), 3.64 (s, 1H), 4.18 (broad m, 1H), 4.52 (s, 2H), 5.12 (s, 2H), 7.18 (d, J=7 Hz, 1H), 7.22–7.38 (broad m, 10H).

EXAMPLE 3

Preparation of
(PhCH$_2$)$_2$CHC(O)—(N-Me)-Val-Tbg-Asp(pyrrolidino)-Asp(cyPn)-γMeLeucinol (Formula 1,
A=2-(phenylmethyl)-3-phenylpropionyl,
B=N-Me-Val, D=Tbg, R$^1$=pyrrolidino, R$^2$ and R$^3$ together with the carbon atom to which they are attached form a cyclopentyl, and E=NHCH(R$^9$)—Z wherein R$^9$ is 2,2-dimethylpropyl and Z=CH$_2$OH)

a) Preparation of the Intermediate Boc-(N-Me)-Val-Tbg-Asp(pyrrolidino)-Asp(cyPn)(Bzl)-NH—(S)—CH{CH$_2$C(CH$_3$)$_3$}CH$_2$OBzl: By following the coupling procedure of example 1, the title compound of example 2 (the first reactant) was coupled with Boc-Asp(pyrrolidino)-OH (the second reactant), described by P. L. Beaulieu et al., European patent application 461,546, published Dec. 18, 1991, to give Boc-Asp(pyrrolidino)-Asp(cyPn)-NH—(S)—CH{CH$_2$C(CH$_3$)$_3$}CH$_2$OBzl. In turn, the latter compound was deprotected (6N HCl/dioxane, 45 min, 4°) and coupled under similar conditions with Boc-Tbg-OH to give Boc-Tbg-Asp(pyrrolidino)-Asp(cyPn)-NH—(S)—CH{CH$_2$C(CH$_3$)$_3$}CH$_2$OBzl. Subsequent removal of the Boc protecting group (6N HCl/dioxane, 4°, 45 min) of the latter compound provided the corresponding free N-terminal amino derivative in the form of its corresponding hydrochloric acid addition salt. Thereafter, the latter amino derivative was coupled under similar conditions with Boc-(N-Me)-Val-OH to give the desired intermediate.

b) Preparation of the title compound: The product of preceding section (a) was converted into its corresponding free N-terminal amino derivative in 6N HCl/dioxane (4°, 45 min). The hydrochloric acid addition salt of the amino derivative (447 mg, 0.490 mmol) was dissolved in CH$_2$Cl$_2$ (1.5 mL). Under an atmosphere of nitrogen, N-methylmorpholine (200 μL, 1.83 mmol) and dibenzylacetyl chloride (269 mg, 1.04 mmol) was added to the solution. The mixture was stirred at room temperature for 7 h. Thereafter, the volatiles were evaporated under reduced pressure. The residue was dissolved in EtOAc. The solution was washed successively with aqueous 1N HCl, a saturated aqueous solution of NaHCO$_3$ and brine, dried (MgSO$_4$) and concentrated under reduced pressure. The residue was dissolved in EtOH (5 mL). The solution was stirred (magnetically) under hydrogen (1 atmosphere) in the presence of 10% (w/w) Pd(OH)$_2$/C (100 mg) for 22 h. The catalyst was collected on a filter and the filtrate was concentrated to dryness. The residue was purified by HPLC on a C-18 reversed-phase column using a gradient of acetonitrile and H$_2$O, each of the solvents containing 0.06% trifluoroacetic acid, to give the title compound as a white solid (220 mg); $^1$H NMR(DMSO-d$_6$, 400 MHz, note that this compound exists as a 4:1 mixture of rotamers in DMSO) δ0.16 (d, J=6.5 Hz, 0.6H), 0.22 (d, J=6.5 Hz, 2.4H), 0.71 (d, J=6.5 Hz, 2.4H), 0.75 (d, J=6.5 Hz, 0.6H), 0.80 (s, 1.8H), 0.82 (s, 7.2H), 0.87 (s, 9H), 1.40–1.55 (m, 7H), 1.65–2.00 (m, 8H), 2.52–3.90 (m, 13H), 2.70 (s, 2.4H), 2.89 (s, 0.6H), 4.21 (d, J=9.5 Hz, 0.8H), 4.34 (d, J=9.5 Hz, 0.2H), 4.43 (d, J=11 Hz, overlap with signal from minor rotomer, 1H), 4.65–4.73 (m, 1H), 4.82 (d, J=10 Hz, overlap with signal from minor rotomer, 1H), 7.04–7.40 (m, 10.8H), 7.57 (d, J=8.5 Hz, 1H), 8.01 (d, J=10 Hz, overlap with signal from minor rotomer, 1H), 8.25 (d, J=9.5 Hz, 0.2H), 8.30 (d, J=7.5 Hz, 0.8H), 8.51 (d, J=7.5 Hz, 0.2H); FAB mass spectrum m/z: 939 (M+Na)$^+$.

EXAMPLE 4

Preparation of Some Representative Intermediates for the Elaboration of the C-Terminus of Peptides of Formula 1.

(a) $NH_2$—(R)—$CH(C_2H_5)C(CH_3)_3$: To a cooled solution (0°) of 4,4-dimethyl-3-pentanone (106 g, 0.928 mol), triethylamine (513 mL, 3.68 mol), and (R)-δ-methylbenzylamine (114 g, 0.940 mol) in dry benzene (1 L), a solution of $TiCl_4$ (50.5 mL, 0,459 mol) in benzene (200 mL) was added at a rate that kept the temperature of the mixture below 10°. Thereafter, the mixture was stirred mechanically for 3 h at 40°, cooled to room temperature and filtered through diatomaceous earth. The diatomaceous earth was washed with $Et_2O$. The combined filtrate and wash was concentrated. The residue was dissolved in dry MeOH (2 L). The solution was cooled to 0° and $NaBH_4$ (20 g, 0.53 mol) was added portionwise while maintaining the temperature of the mixture below 5°. Approximately 2 mL of 10% aqueous HCl was added and the MeOH was evaporated. The residue was dissolved in $Et_2O$. The solution was washed with brine, dried ($MgSO_4$) and evaporated to dryness to give a reddish oil (a 18:1 mixture of diastereoisomers as indicated by NMR). The oil was purified by flash chromatography ($SiO_2$, eluent: EtOAc/hexane, 7:93) to afford N-(1(R)-phenylethyl)-1(R)-ethyl-2,2-dimethylpropylamine as a liquid (110 g, 54%). This material was dissolved in hexane (1.5 L). 6N HCl in dioxane (90 mL) was added to the solution over a period of 15 min. The resulting white solid was collected on a filter and then washed with hexane to provide N-(1(R)-phenylethyl)-1(R)-ethyl-2,2-dimethylpropyl hydrochloride (125 g, 97%). $^1$H NMR($CDCl_3$) δ0.55 (t, J=7.5 Hz, 3H), 1.14 (s, 9H), 1.54–1.95 (m, 2H), 2.23 (d, J=6.5 Hz, 3H), 2.36–2.44 (m, 1H), 4.31–4.49 (m, 1H), 7.30–7.48 (m, 3H), 7.74–7.79 (m, 2H).

A solution of the latter compound (41.5 g) in MeOH (120 mL) was mixed with 10% (w/w) Pd/C (4.0 g) and the mixture was shaken under 50 psi of hydrogen on a Parr hydrogenator at room temperature for 48 h. The mixture was filtered and the filtrate was concentrated to give the desired $NH_2$—(R)—$CH(C_2H_5)C$—$(CH_3)_3$ in the form of its hydrochloric acid addition salt, as a white solid (25 g, 100%). $^1$H NMR($CDCl_3$) δ1.10 (s, 9H), 1.22 (t, J=7 Hz, 2H), 1.58–1.90 (m, 2H), 2.70–2.85 (m, 1H), 8.10–8.40 (broad s, 3H).

In the same manner but replacing 4,4-dimethyl-3-pentanone with 3,3-dimethyl-2-butanone in the preceding procedure, $NH_2$—(R)—$CH(CH_3)C(CH_3)_3$.HCl is obtained.

EXAMPLE 5

Inhibition of Herpes Simplex virus (HSV-1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay

The assay described by P. Gaudreau et al., J. Biol. Chem., 262, 12413 (1987), is used to evaluate the capability of the compounds of this invention to inhibit HSV-1 ribonucleotide reductase activity. Results are expresed as the concentration of the compound producing 50% of the maximal inhibition ($IC_{50}$) of enzyme activity. The number of units of the enzyme preparation used in each assay was constant, based on the specific activity of the enzyme preparation. The results are relative to the activity obtained in control experiments without the test compound and represent the mean of four assays that varied less than 10% with each other.

When $(PhCH_2)_2CHC(O)$—(N-Me)-Val-Tbg-Asp(pyrrolidino)-Asp(cyPn)-γMeLeucinol of example 3 was evaluated according to the preceding assay, the concentration of the compound causing a 50% reduction of the HSV-1 ribonucleotide reductase activity, i.e the $IC_{50}$, was found to be 0.17 μM.

EXAMPLE 6

Inhibition of Herpes Simplex virus (HSV-2) Replication in Cell Culture

Assay:

BHK-21/C13 cells (ATCC CCL 10) are incubated for two days in 150 cm$^2$ T-flasks (1.5×10$^6$ cells/flask) with alpha-MEM medium (Gibco Canada Inc., Burlington, Ontario, Canada) supplemented with 8% (v/v) fetal bovine serum (FBS, Gibco Canada Inc.). The cells are trypsinized and then transferred to fresh media in a 24 well plate to give 2.5×10$^5$ cells in 750 μL of media per well. The cells are incubated at 37° for a period of 6 h to allow them to adhere to the plate. Thereafter, the cells are washed once with 500 μL of alpha-MEM supplemented with 0.5% (v/v) FBS and then incubated with 750 μL of the same media (low serum) for 3 days. After this period of serum starvation, the low serum medium is removed and the cells are incubated in 500 μL of BBMT for 2 to 3 hours. {BBMT medium is described by P. Brazeau et al., Proc. Natl. Acad. Sci. USA, 79, 7909 (1982).} Thereafter, the cells are infected with HSV-2 (multiplicity of infection=0.02 PFU/cell) in 100 μL of BBMT medium. (Note: The HSV-2 used was strain HG-52, see Y. Langelier and G. Buttin, J. Gen. Virol., 57, 21 (1981); the virus was stored at −80°.) Following 1 h of virus adsorption at 37°, the media is removed and the cells are washed with BBMT (3×250 μL). The cells in each well are incubated with or without (control) appropriate concentrations of the test agent dissolved in 200 μL of BBMT medium. After 29 h of incubation at 37°, the infected cells are harvested by first freezing the plate at −80°, followed by thawing. The cells in each well are scraped off the surface of the well with the help of the melting ice fragments. After complete thawing, the cell suspensions are collected and each well is rinsed with 150 μL of BBMT medium. The viral sample (suspension plus washing) is sonicated gently for 4 min at 4°. Cell debris are removed by centrifugation (1000 times gravity for 10 minutes at 4°). The supernatant is collected and stored at −80° until determination of viral titer.

Viral titration was performed by a modification of the colorimetric assay method of M. Langlois et al., Journal of Biological Standardization, 14, 201 (1986), and which is described in detail by R. Déziel and Y. Guindon, supra.

Accordingly, the percentage of virus growth inhibition can be determined for the various concentrations of the test agent, and the concentration of the test agent (i.e. the peptide of formula 1) effecting a 50% inhibition of virus replication, i.e. the $EC_{50}$, can be calculated.

When $(PhCH_2)_2CHC(O)$—(N-Me)-Val-Tbg-AsP(pyrrolidino)-Asp(cyPn)-γMeLeucinol of example 3 was evaluated according to the cell culture assay of this example, the concentration of the compound effecting a 50% inhibition of HSV-2 virus replication, i.e. the $EC_{50}$, was found to be 3 μM.

Other specific examples of compounds of the present invention are as follows:

$(PhCH_2)_2CHC(O)$—(N-Me)-Val-Tbg-Asp (pyrrolidino)-Asp(cyPn)-γMeLeu-OH, having FAB mass spectrum m/z: 932 (M+H)$^+$ and an $EC_{50}$ of 6 μM in the cell culture assay of example 6;

$(PhCH_2)_2CHC(O)$—(N-Me)-Val-Tbg-Asp(pyrrolidino)-Asp(cyPn)-NHCH$_2$C(CH$_3$)$_3$, having FAB mass spectrum m/z: 873 (M+H)$^+$ and an $EC_{50}$ of 1.6 μM in the cell culture assay of example 6;

$(PhCH_2)_2CHC(O)$—(N-Me)-Val-Tbg-Asp(pyrrolidino)-Asp(cyPn)-NH—(R)—CH(C$_2$H$_5$)C(CH$_3$)$_3$, having FAB mass spectrum m/z: 902 (M+H)$^+$ and an $EC_{50}$ of<2 μM in the cell culture assay of example 6;

$(PhCH_2)_2CHC(O)$—(N-Me)-Val-Tbg-Asp(pyrrolidino)-Asp(cyPn)-NH—(R)—CH(CH$_3$)C(CH$_3$)$_3$;

$(PhCH_2)_2CHC(O)$—(N-Me)-Val-Tbg-Asp(pyrrolidino)-Asp(cyPn)-NH—(R)—CH(C$_2$H$_5$)CH$_2$ C(CH$_3$)$_3$; and $(PhCH_2)_2CHC(O)$—(N-Me )-Val-Tbg-Asp(pyrrolidino)-Asp(cyPn)-NH—(R)—CH(CH$_3$)CH$_2$C(CH$_3$)$_3$.

We claim:

1. A peptide of formula 1

wherein

A is a 2-methyl-1-oxopropyl radical disubstituted with phenyl or monosubstituted phenyl wherein the monosubstituent is selected from the group consisting of lower alkyl, halo, hydroxy and lower alkoxy;

B is N(CH$_3$)CHR$^4$C(O) wherein R$^4$ is lower alkyl; D is NH—CHR$^5$C(O) wherein R$^5$ is lower alkyl or a lower alkyl monosubstituted with carboxy, hydroxy, mercapto or benzyloxy;

R$^1$ is lower alkyl, lower cycloalkyl, {1-(lower alkyl)-(lower cycloalkyl)}, or NR$^6$R$^7$ wherein R$^6$ is hydrogen or lower alkyl and R$^7$ is lower alkyl, or R$^6$ and R$^7$ together with the nitrogen atom to which they are attached form a pyrrolidino, piperidino, morpholino or 4-methylpiperazino;

R$^2$ is hydrogen or lower alkyl and R$^3$ is lower alkyl, or R$^2$ and R$^3$ together with the carbon atom to which they are attached form a lower cycloalkyl; and E is NHR$^8$ wherein R$^8$ is (4–9C)alkyl; lower cycloalkyl; lower cycloalkyl monosubstituted or disubstituted with lower alkyl or (lower alkyl)-(lower cycloalkyl); or E is NHCH(R$^9$)—Z wherein R$^9$ is (4–9C)alkyl, lower cycloalkyl or (lower cycloalkyl)-(lower alkyl) and Z is CH$_2$OH, C(O)OH, C(O)NH$_2$ or C(O)OR$^{10}$ wherein R$^{10}$ is lower alkyl;

or a therapeutically acceptable salt thereof.

2. A peptide as defined in claim 1 wherein A is a 2-methyl-1-oxopropyl radical disubstituted with phenyl, 4-(lower alkyl)phenyl, 4-halophenyl or 4-(lower alkyl)phenyl; B is (N-Me)Val, (N-Me)Ile or (N-Me)Tbg; D is amino acid residue of (S)-2-amino-3-hydroxy-3-methylbutyric acid or (R)-2-amino-3-mercapto-methylbutyric acid or an amino acid residue selected from Val, Ile and Tbg; R$^1$ is lower alkyl, lower cycloalkyl, {1-(lower alkyl)-(lower cycloalkyl)}, N,N-dimethylamino, N,N-diethylamino, pyrrolidino or morpholino; R$^2$ and R$^3$ are as defined in claim 1; and E is NHR$^8$ wherein R$^8$ is (4–9C)alkyl; lower cycloalkyl; lower cycloalkyl monosubstituted or disubstituted with lower alkyl; or (lower alkyl)-(lower cycloalkyl); or E is NHCH(R$^9$)—Z wherein R$^9$ is (4–9C)alkyl or (lower cycloalkyl)methyl and Z is as defined in claim 1; or a therapeutically acceptable salt thereof.

3. A peptide as defined in claim 2 wherein A is 2-(phenylmethyl)-3-phenylpropionyl, 2-{(4-fluorophenyl)methyl}-3-(4-fluorophenyl)propionyl, 2-{(4methoxyphenyl)methyl}-3-phenylpropionyl or 2-{(4methoxyphenyl)methyl}-3-(4-methoxyphenyl)propionyl; B is (N-Me)-Val or (N-Me)-Ile; D is Val, Ile or Tbg; R$^1$ is 1-methylethyl, 1,1-dimethylethyl, 1,1-dimethylpropyl, cyclobutyl, cyclopentyl, cyclohexyl, 1-methylcyclopentyl, N,N-dimethylamino, N,N-diethylamino, pyrrolidino or morpholino; R$^2$ is hydrogen and R$^3$ is methyl, ethyl, 1-methylethyl, 1,1-dimethylethyl or propyl, and the carbon atom bearing R$^2$ and R$^3$ has the (R)-configuration, or R$^2$ and R$^3$ each independently is methyl or ethyl, or R$^2$ and R$^3$ together with the carbon atom to which they are attached form a cyclobutyl, cyclopentyl or cyclohexyl; and E is NHR$^8$ wherein R$^8$ is 2,2-dimethylpropyl, 1(R),2,2-trimethylpropyl, 1(R)-ethyl-2,2-dimethylpropyl, 2,2-dimethylbutyl, 3,3-dimethylbutyl, 1(R),2,2-trimethylbutyl, 1(R),3,3-trimethylbutyl, 1(R)-ethyl-3,3-dimethyl or cyclohexylmethyl; or E is NHCH(R$^9$)—Z wherein the carbon atom bearing R$^9$ has the (S)-configuration, R$^9$ is 1,1-dimethylethyl, 1-methylpropyl, 2-methylpropyl, 2,2-dimethylpropyl or cyclohexylmethyl and Z is CH$_2$OH, C(O)OH, C(O)NH$_2$ or C(O)OR$^{10}$ wherein R$^{10}$ is methyl, ethyl or propyl; or a therapeutically acceptable salt thereof.

4. A peptide as defined in claim 3 wherein 2-(phenylmethyl)-3-phenylpropionyl; B is (N-Me)Val; D is Tbg; R$^1$ is 1-methylethyl, 1,1-dimethylethyl, 1-methylpropyl, 1,1-dimethylpropyl, 2,2-dimethylpropyl, cyclobutyl, cyclopentyl, cyclohexyl, 1-methylcyclopentyl, pyrrolidino or morpholino; R$^2$ is hydrogen and R$^3$ is methyl, ethyl, 1-methylethyl or propyl, and the carbon atom bearing R$^2$ and R$^3$ has the (R)-configuration, or R$^2$ and R$^3$ each independently is methyl or ethyl, or R$^2$ and R$^3$ together with the carbon atom to which they are attached form a cyclobutyl, cyclopentyl or cyclohexyl; and E is NHR$^8$ wherein R$^8$ is 2,2-dimethylpropyl, 1(R),2,2-trimethylpropyl, 1(R)-ethyl-2,2-dimethylpropyl, 2,2-dimethylbutyl or 1(R)-ethyl-3,3-dimethylbutyl, or E is NHCH(R$^9$)—Z wherein the carbon atom bearing R$^9$ has the (S)-configuration, R$^9$ is 2,2-dimethylpropyl and Z is CH$_2$OH, C(O)OH, C(O)NH$_2$ or C(O)OR$^{10}$ wherein R$^{10}$ is methyl, ethyl or propyl; or a therapeutically acceptable salt thereof.

5. A peptide as defined in claim 1 selected from the group consisting of:

$(PhCH_2)_2CHC(O)$—(N-Me)-Val-Tbg-Asp(pyrrolidino)-Asp(cyPn)-γMeLeucinol, $(PhCH_2)_2CHC(O)$—(N-Me)-Val-Tbg-Asp(pyrrolidino)-Asp-(cyPn)-γMeLeu-OH, $(PhCH_2)_2CHC(O)$—(N-Me)-Val-Tbg-Asp(pyrrolidino)-Asp(cyPn)-NHCH$_2$C(CH$_3$)$_3$, and $(PhCH_2)_2CHC(O)$—(N-Me)-Val-Tbg-Asp(pyrrolidino)-Asp(cyPn)-NH—(R)—CH(C$_2$H$_5$)C(CH$_3$)$_3$.

6. A pharmacetical composition comprising an anti-herpes virally effective amount of a peptide as defined in claim 1, or a therapeutically acceptable salt thereof, and a pharmaceutically or veterinarily acceptable carrier.

7. A pharmaceutical composition of claim 6 wherein the peptide is selected from the group consisting of:

(PhCH$_2$)$_2$CHC(O)—(N-Me)-Val-Tbg-Asp(pyrrolidino)-Asp(cyPn)-γMeLeucinol, (PhCH$_2$)$_2$CHC(O)—(N-Me)-Val-Tbg-Asp(pyrrolidino)-Asp-(cyPn)-γMeLeu-OH, (PhCH$_2$)$_2$CHC(O)—(N-Me)-Val-Tbg-Asp(pyrrolidino)-Asp(cyPn)-NHCH$_2$C(CH$_3$)$_3$, and (PhCH$_2$)$_2$CHC(O)—(N-Me)-Val-Tbg-Asp(pyrrolidino)-Asp(cyPn)-NH—(R)—CH(C$^1$H $_5$)C(CH$_3$)$_3$.

8. A cosmetic composition comprising a peptide as defined in claim 1, or a therapeutically acceptable salt thereof, and a physiologically acceptable carrier suitable for topical application.

9. A method of treating a herpes viral infection in a mammal comprising administering to the mammal an anti-herpes virally effective amount of a peptide as defined in claim 1, or a therapeutically acceptable salt thereof.

10. A method of claim 9 wherein the peptide is selected form the group consisting of:

(PhCH$_2$)$_2$CHC(O)—(N-Me)-Val-Tbg-Asp(pyrrolidino)-Asp(cyPn)-γMeLeucinol, (PhCH$_2$)$_2$CHC(O)—(N-Me)-Val-Tbg-Asp(pyrrolidino)-Asp-(cyPn)-γMeLeu-OH, (PhCH$_2$)$_2$CHC(O)—(N-Me)-Val-Tbg-Asp(pyrrolidino)-Asp(cyPn)-NHCH$_2$C(CH$_3$)$_3$, and (PhCH$_2$)$_2$CHC(O)—(N-Me)-Val-Tbg-Asp(pyrrolidino)-Asp(cyPn)-NH—(R)—CH(C$_2$H$_5$)C(CH$_3$)$_3$.

11. A method of inhibiting the replication of herpes virus by contacting the virus with a herpes viral ribonucleotide reductase inhibiting amount of a peptide as defined in claim 1, or a therapeutically acceptable salt thereof.

12. A method of claim 11 wherein the peptide is selected from the group consisting of:

(PhCH$_2$)$_2$CHC(O)—(N-Me)-Val-Tbg-Asp(pyrrolidino)-Asp(cyPn)-γMeLeucinol, (PhCH$_2$)$_2$CHC(O)—(N-Me)-Val-Tbg-Asp(pyrrolidino)-Asp-(cyPn)-γMeLeu-OH, (PhCH$_2$)$_2$CHC(O)—(N-Me)-Val-Tbg-Asp(pyrrolidino)-Asp(cyPn)-NHCH$_2$C(CH$_3$)$_3$, and (PhCH$_2$)$_2$CHC(O)—(N-Me)-Val-Tbg-Asp(pyrrolidino)-Asp(cyPn)-NH—(R)—CH(C$_2$H$_5$)C(CH$_3$)$_3$.

13. A method of treating herpes simplex virus type 1, or type 2, infections in a mammal comprising administering thereto an effective amount of the pharmaceutical composition of claim 6 wherein the peptide of the composition is (PhCH$_2$)$_2$CHC(O)—(N-Me)-Val-Tbg-Asp(pyrrolidino)-Asp(cyPn)-γMeLeucinol.

14. A process for preparing a peptide as defined in claim 1, or a therapeutically acceptable salt thereof, comprising:

a) stepwise coupling, in the order of the sequence of the peptide, of the amino acid or derived amino acid residues, and non-peptidic fragments of the peptide, in which i) reactive side chain groups of the residue or fragments are protected with suitable protective groups to prevent chemical reactions from occurring at that site until the protective group is ultimately removed after the completion of the stepwise coupling;

ii) an α-amino group of a coupling reactant is protected by an α-amino protective group while the free carboxy group of that reactant couples with the free α-amino group of the second reactant; the α-amino protective group being one which can be selectively removed to allow the subsequent coupling step to take place at that α-amino group; and iii) the C-terminal carboxyl of the amino acid residue of the amino acid residue or peptide fragment, which is to become the C-terminal function of the protected peptide, if present, is protected with a suitable protective group which will prevent chemical reaction occurring at that site until after the desired amino acid sequence for the peptide has been assembled; and b) at the completion of the coupling, eliminating any protecting groups and, if required, effecting standard transformations to obtain the peptide of claim 1; and if desired, converting the peptide into a therapeutically acceptable salt.

* * * * *